United States Patent [19]

Yanagisawa et al.

[11] Patent Number: 5,155,008

[45] Date of Patent: Oct. 13, 1992

[54] OPTICAL RECORDING MEDIUM

[75] Inventors: Shuichi Yanagisawa; Tatsuro Sakai; Fumio Matsui, all of Saitama; Tsuneki Okazaki; Akira Shimpo, both of Okayama, all of Japan

[73] Assignee: Pioneer Electronic Corporation, Tokyo, Japan

[21] Appl. No.: 570,450

[22] Filed: Aug. 21, 1990

[30] Foreign Application Priority Data

Dec. 29, 1989 [JP] Japan ................................. 1-341642

[51] Int. Cl.$^5$ .............................................. G03C 1/72
[52] U.S. Cl. .................................... 430/270; 430/495; 430/945; 346/135.1
[58] Field of Search ............... 430/495, 270, 271, 275, 430/276, 945; 346/135.1

[56] References Cited

U.S. PATENT DOCUMENTS

| 4,626,496 | 12/1986 | Sato | 430/495 |
| 4,652,514 | 3/1987 | Abe et al. | 430/343 |
| 4,713,314 | 12/1987 | Namba et al. | 430/270 |
| 4,957,854 | 9/1990 | Oguchi et al. | 430/270 |

FOREIGN PATENT DOCUMENTS 0201243  11/1984  Japan ................................. 430/270

Primary Examiner—Lee C. Wright
Attorney, Agent, or Firm—Sughrue, Mion, Zinn, Macpeak & Seas

[57] ABSTRACT

An optical recording medium having a recording layer containing a particular cyanine dye matter and a particular quencher. The material of the recording medium can be directly applied to the injection-molded substrate without any damage to the substrate. The productivity of this recording medium is therefore high. This medium also has superior recording/reproduction characteristics.

1 Claim, No Drawings

OPTICAL RECORDING MEDIUM

BACKGROUND OF THE INVENTION

This invention relates to optical recording mediums and, more particularly, to an optical recording medium having a recording layer containing an organic coloring matter.

Ordinarily, optical recording mediums have superior characteristics; they have a large storage capacity and are capable of effecting writing or reading in a non-contact manner. Optical recording mediums have therefore been developed extensively.

A write once type optical disk is known as an example of optical recording mediums. This type of optical disk is used in such a manner that a laser beam is condensed to a very small area on a recording layer and is converted into thermal energy to change the state of the recording layer (forming pits) thereby to write data, and that the corresponding data is reproduced in accordance with changes in the quantity of light reflected on recording portions and non-recording portions.

Rreferably, the recording layer of such a medium is formed of a material capable of achieving a large change in reflectivity. Low melting point metallic materials containing tellurium have previously been used to form the recording layer.

Recently, however, optical recording medium having a recording layer formed of an organic material mainly constituted by a coloring matter have been proposed for use in place of tellurium materials because tellurium materials are toxic, and because it is necessary to improve the sensitivity of medium and to reduce the manufacture cost. (Examples of such mediums are disclosed in Japanese Patent Laid-Open Publication Nos. 58-112790, 58-114989, 58-125246 and 60-71295.)

In general, an optical recording medium having a recording layer formed of an organic material mainly constituted by a coloring matter has a substrate, an ultraviolet-curing resin layer (Photo-Polymer layer) formed on the substrate to form grooves and addresses, and a recording layer formed on the ultraviolet-curing resin layer by spin coating.

The substrate having the Photo-Polymer layer is formed as described below. The ultraviolet-curing resin is dropped on, for example, a Ni stamper, the substrate is placed thereon, and the ultraviolet curing resin is spread so as to have a sufficiently small thickness while preventing formation of bubbles between the stamper and the substrate. Thereafter, the ultraviolet curing resin is irradiated with ultraviolet rays through the substrate to be polymerized and cured. Therefore the process for forming this substrate is complicated and troublesome and it is difficult to improve the productivity. To avoid these problems, an injection-molded substrate may be used which is a plastic substrate integrally formed with grooves and so on by injection molding without using any ultraviolet-curing resin.

This injection-molded substrate, however, cannot be used in practice because it has a recording layer directly formed by coating on its surface (on the groove side) and is therefore damaged generally by a solvent contained in the coating liquid.

SUMMARY OF THE INVENTION

In view of the above-described problems, an object of the present invention is to provide an optical recording medium which is formed without damaging the injection-molded substrate and which has a recording layer improved in recording/reproduction characteristics.

To achieve this object, according to the present invention, there is provided an optical recording medium having a plastic substrate and a recording layer formed on the plastic substrate, the recording layer containing a cyanine dye expressed by the following general formula:

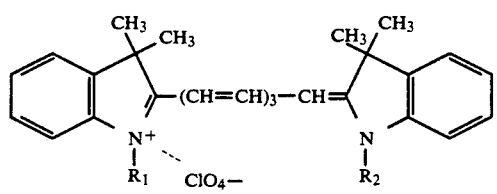

(where $R_1$ and $R_2$ respectively represent alkyl groups having 2 to 4 carbon atoms), and a quencher expressed by the following general formula:

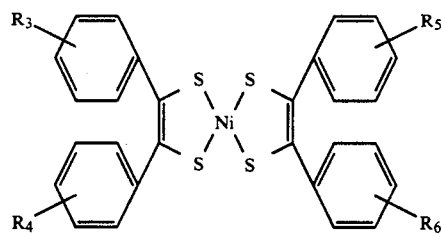

(where $R_3$, $R_4$, $R_5$ and $R_6$ respectively represent hydrogen or substituent groups).

DETAILED DESCRIPTION OF THE INVENTION

An injection-molded substrate is used as the plastic substrate in accordance with the present invention to improve the productivity. The injection-molded substrate is formed in such a manner that material is integrally molded by one-shot injection molding into a flat plate like substrate with grooves, addresses and so on formed on one surface of the substrate.

This substrate is formed of a plastic material such as a polycarbonate (PC) resin or a polymethylmethacrylate (PMMA) resin.

A recording layer is formed on this substrate. The recording layer contains a cyanine dye expressed by the following general formula [I]:

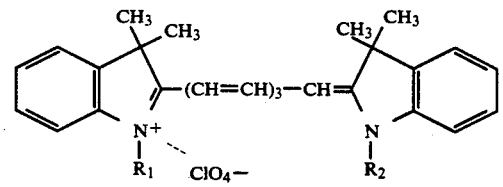

In the general formula [I], $R_1$ and $R_2$ respectively represent alkyl groups having 2 to 4, more preferably 2 to 3 carbon atoms. If the number of carbon atom is smaller than 2, the solubility of the cyanine dye in a solvent described later is poor, resulting in failure to form the layer. If the number of carbon atoms is larger than 4, the solubility is also poor and it is not possible to form the layer on the substrate.

The recording layer in accordance with the present invention further contains a quencher expressed by the following general formula [II]:

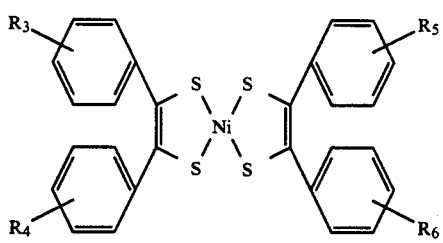

In the general formula [II], $R_3$, $R_4$, $R_5$ and $R_6$ respectively represent hydrogen or substituent groups substituted for hydrogen.

Each substituent group is, for example, $CH_3O-$, $CH_3OCH_2CH_2O-$, $CH_3COO-$, $(n-C_3H_7)_2N-$, $(C_2H_5)_2N-$, or $Cl-$.

Such a quencher may be selected from compounds expressed by the following structural formula:

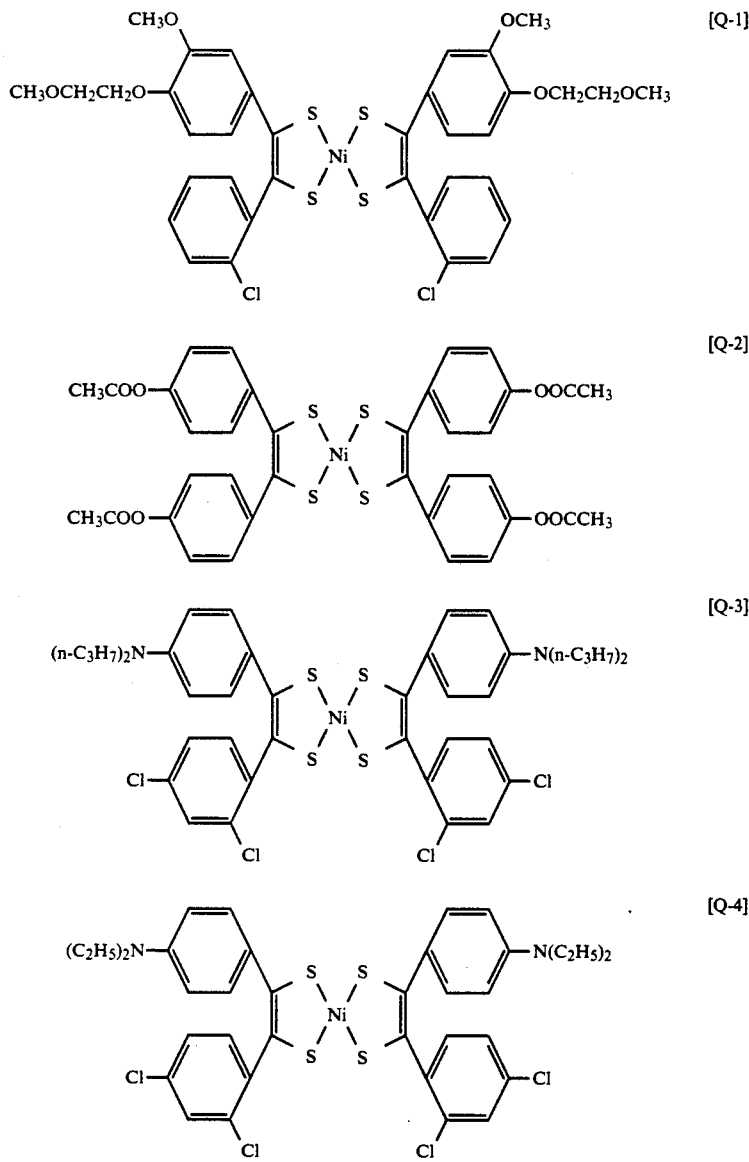

Specifically, among these quenchers, the one expressed by the structural formula [Q-1] is preferred in terms of medium characteristics substrated on the combination with the cyanine dye expressed by general formula [I]. The quencher is used to increase the photostability of the cyanine dye and, in particular, to prevent decoloring (reproduction deterioration) caused by reading light. The quencher is contained in an amount of 5 to 50 mole with respect to 100 mole of the cyanine dye.

The recoring layer containing this quencher and the above-described cyanine dye is formed by the ordinary means, e.g., the spin coating method. The thickness of the formed recording layer is about 40 to 100 nm. A solvent used for coating may be, for example, diacetone alcohol, ethyl CELLOSOLVE (2-ethoxyethanol), methyl CELLOSOLVE (2-methoxyethanol), isophorone or methanol. These solvents are suitable because they do not damage the substrate on which the recording layer is formed.

The laser light applied to the recording medium in accordance with the present invention is selected according to the wavelength of light absorbed by the cyanine dye contained in the recording layer. Specifically, semiconductor laser light (wavelength: 760 to 830 nm) is preferred.

As described above, the recording medium in accordance with the present invention is formed of an injection-molded substrate and recording layer formed on the substrate. Ordinarily, however, it is preferable to adapt an air sandwich structure in which two medium sheets of this type are disposed so that the recording layer surface opposed to each other.

Ordinarily, the medium in accordance with the present invention is irradiated with pulses of recording light while being rotated.

Portions of the recording layer are thereby melted and removed to form pits.

The pits formed in this manner are read by detecting change in the reflection of reading light while the medium is being rotated.

EXPERIMENTAL EXAMPLE

The present invention will be described below in more detail with respect to examples thereof.

Each of compounds [D-1] to [D-6] shown below was used as a coloring matter to be contained in the recording layer. The above-mentioned compound [Q-1] or a compound [Q*] shown below was used as a quencher. The quencher was contained in an amount of mole with respect to 7 mole of the coloring matter. These compounds were dissolved in a solvent as shown in Table 1. The solution liquid thereby prepared was applied to a polycarbonate (PC) resin substrate having a diameter of 13 cm to form a layer having a thickness of 60 nm. Various optical recording medium samples were formed in this manner.

Coloring Matter

[D-1]
Each of $R_1$ and $R_2$ in general formula [I] is $C_2H_5$ (ethyl group)

[D-2]
Each of $R_1$ and $R_2$ in general formula [I] is $C_3H_7$ (propyl group)

[D-3]
Each of $R_1$ and $R_2$ in general formula [I] is $C_5H_{11}$ (pentyl group)

[D-4]
Each of $R_1$ and $R_2$ in general formula [I] is $CH_3$ (methyl group)

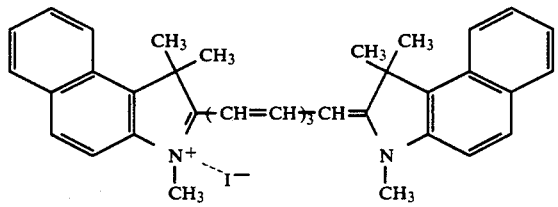

[D-5]

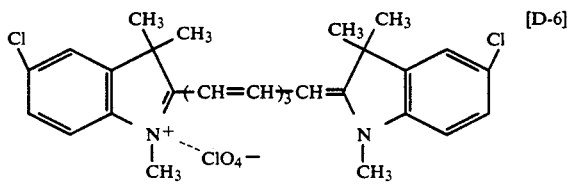

[D-6]

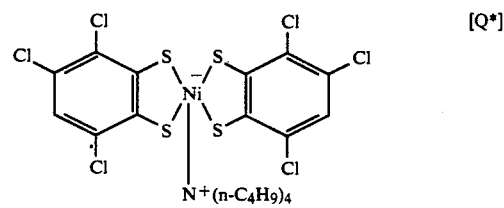

[Q*]

Table 1 shows the contructions of optical recording medium samples formed in the above-described manner and the results of evaluation of these samples.

Evaluation items were as follows: the solubility of the coloring matter and the quencher; the change in the level of a system control signal in a high-temperature/high-humidity environment (at 70° C. and at 90% RH); the change in recording/reproduction characteristics under the same condition; and repeated reading characteristics determined by the number of reading repeating times. Overall characteristics substrated on these characteristics were also evaluated.

These evaluation results are shown in Table 1.

TABLE 1

| Sample No. | Coloring matter | Quencher | Solvent | Substrate | solubility | High-temperature high-humidity (70° C. 90% RH) | | Repeated reading | Overall characteristics |
| | | | | | | System control signal | Recording/reproduction characteristics | | |
| --- | --- | --- | --- | --- | --- | --- | --- | --- | --- |
| No. 1 (present invention) | D-1 | Q-1 | methyl CELLOSOLVE | PC | ○ | ⊚ | ⊚ | ⊚ | ⊚ |
| No. 2 (present invention) | D-1 | Q-1 | diacetone alcohol | PC | ○ | ○ | ○ | ○ | ○ |
| No. 3 (present invention) | D-2 | Q-1 | methyl CELLOSOLVE | PC | ○ | ⊚ | ⊚ | ⊚ | ⊚ |
| No. 4 (present invention) | D-2 | Q-1 | diacetone alcohol | PC | ○ | ○ | ○ | ○ | ○ |
| No. 5 (comparison example) | D-1 | Q* | methyl CELLOSOLVE | PC | ○ | ○ | x | ⊚ | x |
| No. 6 (comparison example) | D-2 | Q* | methyl CELLOSOLVE | PC | ○ | ○ | x | ⊚ | x |
| No. 7 (comparison example) | D-3 | Q-1 | methyl CELLOSOLVE | PC | x | — | — | — | — |
| No. 8 (comparison example) | D-4 | Q-1 | methyl CELLOSOLVE | PC | x | — | — | — | — |
| No. 9 (compari- | D-5 | Q-1 | methyl CELLOSOLVE | PC | ○ | Δ | x | x | x |

TABLE 1-continued

| Sample No. | Coloring matter | Quencher | Solvent | Substrate | solubility | High-temperature high-humidity (70° C. 90% RH) System control signal | Recording/reproduction characteristics | Repeated reading | Overall characteristics |
| --- | --- | --- | --- | --- | --- | --- | --- | --- | --- |
| son example) | | | | | | | | | |
| No. 10 (comparison example) | D-6 | Q* | methyl CELLOSOLVE | PC | x | — | — | — | — |
| No. 11 (comparison example) | D-6 | Q* | dichloroethane | PMMA + UV curing resin | ○ | ⊚ | ⊚ | ⊚ | ⊚ |

Evaluation criteria
⊚ very good
○ good
Δ unsatisfactory on practical level
x unusable on practical level The material of the substrate of the sample No. 11 is different from those of the samples No. 1 to No. 10; the substrate of sample No. 11 comprises a combination of PMMA and an ultraviolet-curing resin layer (Photo-Polymer layer).

The effects of the present invention are apparent from the foregoing. That is, the optical recording medium in accordance with the present invention has a recording layer containing a particular cyanine dye and a particular quencher. The material of the recording layer can therefore be directly applied to the injection-molded substrate without any damage to the substrate, thereby achieving a remarkable improvement in productivity in comparison with a medium having a substrate formed of the conventional ultraviolet curing resin layer (Photo-Polymer layer). Moreover, the medium of the present invention has superior recording/reproduction characteristics.

What is claimed is:

1. An optical recording medium comprising a plastic substrate and a recording layer directly formed on the plastic substrate, said plastic substrate consisting of an injection-molded substrate made of polycarbonate resin with grooves, said recording layer being formed by coating a coating liquid containing a cyanine dye expressed by the following structural formula:

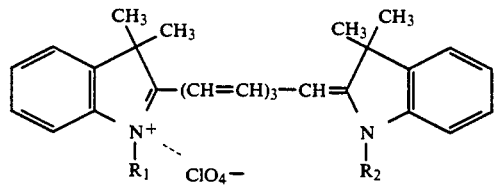

wherein $R_1$ and $R_2$ each represents a straight or branched alkyl group having 2 to 3 carbon atoms, a quencher expressed by the following structural formula:

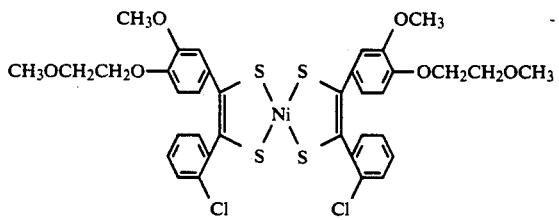

and at least one solvent selected from the group consisting of 2-methoxyethanol, diacetone alcohol and 2-ethoxyethanol.

* * * * *